United States Patent
Seng et al.

[11] Patent Number: 5,683,741
[45] Date of Patent: Nov. 4, 1997

[54] METHOD FOR THE QUALITY-CONTROLLED FINISHING OF A SURFACE WITH A RADIATION-CURED SURFACE FINISH

[75] Inventors: Hans-Peter Seng, Berlin; Reiner Mehnert, Markkleeberg; Hans-Rüdiger Döring, Leipzig, all of Germany

[73] Assignees: Druckfarbenfabrik Gebr.Schmidt GmbH, Frankfurt; Brucker-Saxonia Analytik GmbH, Leipzig, both of Germany

[21] Appl. No.: 442,942

[22] Filed: May 17, 1995

[30] Foreign Application Priority Data

May 18, 1994 [DE] Germany .................. 44 17 366

[51] Int. Cl.⁶ .................. B05D 1/00; C08J 7/04; H01J 49/00
[52] U.S. Cl. .................. 427/8; 427/496; 427/508; 427/519; 427/520; 427/511; 427/504; 250/282
[58] Field of Search ............. 427/8, 487, 496, 427/508, 519, 520, 498, 500, 504, 512, 510, 514, 511; 250/286, 287, 282, 283

[56] References Cited

U.S. PATENT DOCUMENTS

| | | |
|---|---|---|
| 4,195,513 | 4/1980 | Cohen . |
| 4,469,623 | 9/1984 | Danielson et al. .............. 252/408.1 |
| 4,551,624 | 11/1985 | Spangler et al. .............. 250/287 |
| 4,920,578 | 5/1990 | Kerr, III .............. 427/517 |
| 5,021,654 | 6/1991 | Campbell et al. .............. 250/287 |
| 5,083,019 | 1/1992 | Spangler .............. 250/286 |
| 5,135,297 | 8/1992 | Valint, Jr. .............. 427/512 |
| 5,156,780 | 10/1992 | Kenigsberg et al. .............. 427/513 |
| 5,162,652 | 11/1992 | Cohen et al. . |
| 5,213,875 | 5/1993 | Su et al. .............. 427/520 |
| 5,218,203 | 6/1993 | Eisele et al. .............. 250/287 |
| 5,338,931 | 8/1994 | Spangler et al. .............. 250/287 |
| 5,420,424 | 5/1995 | Carnahan et al. .............. 250/287 |
| 5,457,316 | 10/1995 | Cohen et al. .............. 250/286 |
| 5,465,607 | 11/1995 | Corrigan et al. .............. 250/282 |

FOREIGN PATENT DOCUMENTS

| | | |
|---|---|---|
| 0027748 | 4/1981 | European Pat. Off. . |
| 4222576 | 1/1994 | Germany . |
| 1338157 | 11/1973 | United Kingdom . |

OTHER PUBLICATIONS

Brushwell, William: Strahlungshärtende Beschichtungen. In: farbe + lack, 84.Jg., 1/1978, S.27,28 German No Translation.

Kirchmayr, Rudolf, u.a.: Photointiatoren für die UV-Härtung von Lacken. In: farbe + lack, 86.Jg., 3/1980, S.224–230 –german–no translation.

G. Arnold, H.R. Döring "Ionenbeweglichkeitsspektrometrie", ZFI-Mitteilungen No. 154 (Zentralinstitut für Isotopen–und Strahlenforschung der Akademie der Wissenschaften der DDR) Leipzig (1190), 13–35 Apr. 1990 German–No Translation.

Tagungsband 17. Münchener Klebstoff–und Veredelungsseminar 1992, ed. Prof. Dr. Nitzl, Fachhochschule Müchen German –no translation.

*Primary Examiner*—Marianne Padgett
*Attorney, Agent, or Firm*—Sprung Horn Kramer & Woods

[57] ABSTRACT

Method for the quality-controlled treatment of surfaces with a radiation-cured surface treatment, in which a finishing formulation is applied to the surface and is polymerically crosslinked under the effect of radiation. To enable the quality control to be conducted non-destructively and at reduced cost, it is proposed that the finishing formulation contains a proton-affinitive indicator substance analyzable by ion mobility spectroscopy and that the indicator substance escaping from the printed or coated surface after the radiation curing is analyzed by means of ion mobility spectroscopy.

27 Claims, 2 Drawing Sheets

METHOD FOR THE QUALITY-CONTROLLED FINISHING OF A SURFACE WITH A RADIATION-CURED SURFACE FINISH

BACKGROUND OF THE INVENTION

The invention relates to a method for the quality-controlled finishing of surfaces with a polymeric surface treatment, in which a radiation-curing finish formulation is applied to the surface and is polymerically crosslinked under the effect of radiation. Thereby the finish is cured.

The finishing with a finish formulation can be effected by printing techniques, in particular by printing of the surface with printing inks. In addition, however, the method according to the invention also relates to other forms of surface finishing, in particular to the application of a radiation-curable clear lacquer. The latter is a common means e.g. for protecting packages already printed on. Such clear lacquer coats differ from coloured prints mainly in that, unlike printing inks, they do not contain pigments. Printing by means of radiation-curing printing inks is used as an example below. This must not be interpreted, however, as limiting the general applicability of the invention, which also covers the application of pigmented or pigment-free surface treatments by printing or other application methods, in particular in a layer thickness range between 0.1 and 200 μm.

Radiation-curing printing ink formulations are used for many applications, for example package printing. Monomers or oligomers that polymerize and crosslink under the action of UV or electron beam radiation form essential components of their binder system. A particularly resistant print surface is therefore also obtained on problematical surfaces, for example on aluminium coatings. In particular treatment formulations based on acrylic and epoxy resins are conventional. Because of their useful properties, radiation-curing printing inks have been of great importance for the last twenty years. Other fields of application of the instant invention, in addition to the printing industry, include the wood processing industry, e.g. finishing of parquet flooring elements.

The quality of a radiation-cured printing ink layer depends crucially on its content of non-crosslinked migrating components (monomers or oligomers). The total content of these migrating components in a layer is described as the "global migration".

The degree of crosslinking and the resulting remaining amount of migrating substances are critical for the mechanical resistance and the overall properties of the coat. Reliable monitoring of the coat quality is also essential given the health risks which may arise from an insufficient degree of crosslinking in certain applications (food packaging). A wide range of quality control methods have therefore been proposed.

High pressure liquid chromatography (HPLC) analysis in particular has been used in the past. In this the non-crosslinked components are extracted in liquid form from a sample of the printed material, e.g. by methanol in an ultrasonic bath, and then analysed by the HPLC method. In another conventional method a sample of the printed material is heated to a relatively high temperature of say 80° C. and the substances released from the coat are examined in the gas phase by gas chromatography (in particular by GC head space analysis).

These known methods have disadvantages, however, because they are destructive, i.e. they require to take a sample from the printed material. The sample is destroyed during the testing. In addition the known methods of analysis require expensive equipment.

SUMMARY OF THE INVENTION

The object of the invention is therefore to allow the quality checking of a radiation-cured surface finish (in particular printing ink coats) to be carried out reliably at reduced expense.

Accordingly the invention provides a method for the quality-controlled finishing of a surface with a radiation-cured surface finish, in which a finishing formulation is applied to the surface and is polymerically cross-linked under the effect of radiation, wherein the finishing formulation contains a proton-affinitive indicator substance analysable by ion mobility spectroscopy and the indicator substance escaping from the printed surface after the radiation curing is analysed by means of ion mobility spectroscopy.

Ion mobility spectroscopy (IMS) is a method of analysis in which the molecules of the substance which is to be analysed (analyte) are ionised chemically at atmospheric pressure to form molecule ions. The latter are then segregated physically in a drift chamber according to their mobility by means of an electric field.

Ion mobility spectrometers are used for analysis by the IMS method. These consist mainly of an ion source, an ion inlet gate and a drift chamber with a collector electrode (collector) plus the measurement electronics. The analyte molecules are sucked into the ion source by a carrier gas, which is usually air. In the ion source the carrier gas molecules are ionised by irradiation with beta-particles from a tritium radiation source or $Ni^{63}$ source to from so-called reaction ions. If air is the carrier gas, these are mainly the ions $(H_2O)_6H^+$ or $(H_2O)_3O_2^-$. In the reaction chamber adjoining the ion source the reaction ions react with the analyte molecules and form so-called product ions, i.e. ionised molecules.

The ion source, the reaction chamber and the drift chamber generally take the form of a straight tube, to which an electric field is applied. This field transports the product ions (plus unreacted reaction ions) along the tube in the direction of the collector. At the inlet of the drift chamber there is an ion inlet gate, which is opened, for example, every 30 msec for approximately 300 μsec. The ion cloud entering the drift chamber is split up during its passage through the drift chamber in accordance with the mobility of the individual ions in the electric field. On striking the collector, each ionic species of identical mobility generates an electric peak. The peaks taken together make up the ion mobility spectrum.

The mass of the molecule ions, i.e. their molecular weight, is the main determinant of their mobility. In addition, however, the molecular structure has to be considered. The position of the peaks along the drift time axis of the spectrum is thus an indication of the mobility of the product ions, and the area of the peak is a measure of their quantity, i.e. the concentration of product ions with identical mobility.

Further details of the IMS method—i.e. both the equipment and the chemical-physical aspects—are found in the relevant literature. A summary is given, for example, in: G. Arnold, H. R. Döring "Ionenbeweglichkeitsspektrometrie", ZFI-Mitteilungen No. 154 (Zentralinstitut für Isotopen- und Strahlenforschung der Akademie der Wissenschaften der DDR) Leipzig (1990), 1–35, with many other literature references.

Although the IMS method aroused great scientific interest in the seventies, its range of application for chemical analysis proved to be very limited. Its main use is for detecting organic phosphorus industrial toxins, explosives and drugs, and for detecting weaponry in the military field. Portable ion mobility spectrometers are available for such applications, such as the product RAID-1 of Bruker-Saxonia-Analytic-GmbH, Leipzig, Germany.

A paper on the uses of ion mobility spectroscopy for analysing traces of migrating components in radiation-cured printing inks was published in Tagungsband 17. M ünchener Klebstoff- und Veredelungsseminar 1992, ed. Prof. Dr. Nitzl, Fachhochschule München. Here various electron-affinitive test substances that are conventional monomers of electron beam-radiation-curing printing ink preparations are analysed by the IMS method as a function of the radiation dose. The results show a rise in the monomer concentration with increasing radiation dose. This result does not correspond to the actual conditions. It is clear both from analyses with conventional methods and from experience in the field that the crosslinking increases with increasing radiation dose and the monomer concentration decreases correspondingly. The author himself expresses doubts at the end of his paper about whether the IMS method is suitable for analysing traces of migrating components in radiation-cured printing inks.

According to the present invention, printing ink formulations whose quality is to be checked by the IMS method contain a proton-affinitive indicator substance. Preferably the proton affinity of the latter is higher than that of water (707 kJ/mol). Particularly preferably the proton affinity must be far greater than that of water, wherein values above 750 kJ/mol, in particular above 800 kJ/mol, are particularly indicative of suitability as an indicator substance in preparations for a radiation-curing surface finish. It can be assumed that under these circumstances a proton transfer between the reaction ions R and the ions M of the indicator substance takes place according to the formula

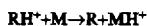

Surprisingly it has been found that the concentration of the indicator substance in the finishing formulation should not exceed specific maximum values. It should be calculated so that the equilibrium concentration of the indicator substance in the gas phase directly above the printed and cured surface comes to not more 10 mg/m$^3$, preferably not more than 1 mg/m$^3$. Optimum use is thus made of the dynamic range of the IMS method within the scope of the invention. It has been found in practice that the concentration of the indicator substance in the finishing formulation should not amount to more than 2%, preferably not more than 1%, particularly preferably not more than 0.5%.

In particular for radically or radically/cationically (hybrid) curing printing inks components of the initiator system have proved to be suitable indicator substances. The role of the initiator system in the printing ink formulation is to initiate the crosslinking polymerisation. It can consist of only one compound, namely a photoinitiator, or of at least two substances reacting and interacting with one another on initiation of the polymerisation. Since the binder of the printing ink consists of an initiator system, monomers and (optionally) oligomers, these substances are often called collectively the binding system.

A photoinitiator is necessary in particular with UV radiation curing. It consists of molecules that are brought into an excited state under the effect of UV radiation. Radically curing printing ink preparations make use of photoinitiators that form a pair of radicals under the effect of UV radiation. These radicals initiate among the monomers and oligomers of the printing ink preparation a crosslinking chain reaction that produces a crosslinked and hence cured polymer surface layer.

Where initiator systems consist of several substances, the (UV or electron) radiation brings one molecule to an excited intermediate state, e.g. a relatively stable triplet state, which does not itself result in the formation of radicals. Instead, a further substance is present, namely a so-called co-initiator, which reacts with the first molecule in the excited state (triplet state) and forms a pair of radicals. The co-initiator in such a system for initiating crosslinking is especially suitable as an indicator substance for the present invention.

Photoinitiators and co-initiators (generally components of the initiator system) are particularly suitable as indicator substances for the non-destructive quality testing of a surface finish applied by printing. This is all the more surprising because these substances are present in the overall formulation in only relatively small concentrations of some 5%. The residual content of these substances in the finished surface treatment is even lower, given that the components of the initiator system are almost completely crosslinked during polymerisation. The concentration in the finished surface treatment amounts to a few ppm. Nevertheless these substances present in extremely small concentrations have proved to be suitable indicators of the quality of the surface treatment.

In order that the indicator substance may be present in the small concentration preferred with the method according to the invention, it is even preferable in many cases for the finishing formulation to comprise two initiator systems, namely a first initiator system containing a photoinitiator or co-initiator of high proton affinity capable of being analysed by the IMS method, and a second initiator system without any components of such high proton affinity. The proton affinity of all the components of the second initiator system should be at least 10% below that of the indicator substance. By using two initiator systems, it is possible firstly for the indicator substance to be in the desired small concentration of less than 2%, preferably less than 1%, and secondly for the total content of initiator substances in the formulation to reach the usual level (usually about 5%) for ensuring sufficiently complete crosslinking.

Indicator substances for the present invention can have extremely varied chemical structures. The indicator substance for radically or radically/cationically curing printing inks can for example be a benzoin, benzoin ether, benzil ketal, thioxanthone derivative, α,α-,dialkoxyacetophenone derivative, α-hydroxyalkyl-phenone, α-aminoalkylphenone derivative, acrylophosphine oxide, benzophenone or a benzophenone derivative. The substances 2-hydroxy-2-methyl-1-phenyl-propan-1-one or 1-(4-isopropylphenyl)-2-hydroxy- 2-methyl-propan-l-one have proved particularly effective in practice.

Other advantageous substance groups are amino acrylates, co- polymerisable amines and alkyl amines.

As cationically curing printing inks there are suitable, according to current scientific knowledge, alkene carbonates, in particular propylene carbonate, as well as arylsulphonium salts, aryliodonium salts and vinyl ethers.

The molecular weight of the indicator substance should preferably be between 50 and 400.

The invention will be explained in detail below by means of embodiments shown diagrammatically in the figures, where

DETAILED DESCRIPTION OF THE INVENTION

Figure 1:
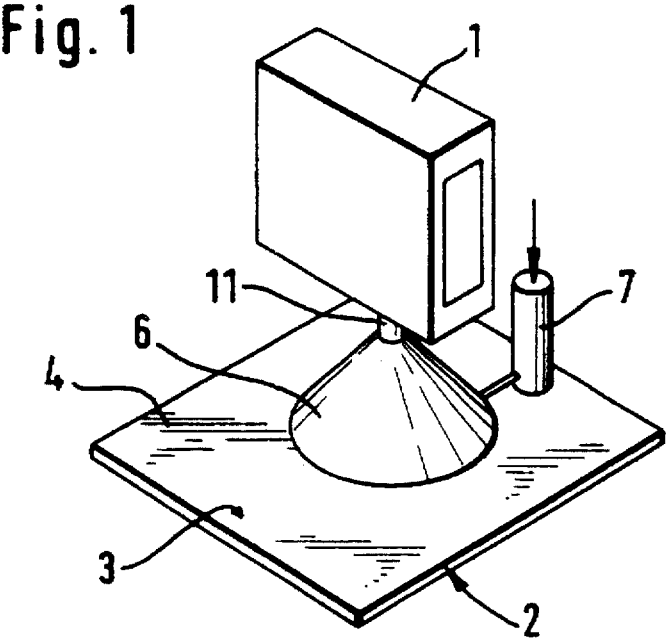
FIG. 1 is a perspective overall view of a measurement setup according to the invention.

FIG. 1 shows an ion mobility spectrometer 1 that is located in the measurement position above a printed article 2, to whose surface 3 a radiation-cured surface finish (in particular a print layer) 4 is applied, the quality of which is to be tested. A suction head 6 is connected to the analysis gas inlet 11 of the ion mobility spectrometer 1. The suction head 6 has in the case shown the form of a truncated cone, whose lower edge delimiting the greater cone opening (suction opening) rests on the surface 3 of the printed article 2. In order to ensure the plane support of the suction opening of the suction head 6 on the surface 3, the printed article lies& at the measurement point on a plane support element (not shown). The upper, smaller opening of the suction head 6 is connected in a gas-tight manner to the analysis gas inlet 11 of the spectrometer 1. The suction head 6 can naturally also be of different construction, provided that on the one hand the gas-tight connection to the spectrometer is ensured and on the other its inner volume is connected over a sufficiently large exchange area to the print layer that is to be quality-tested.

The inner space of the suction head 6 is connected via a lateral connection to an activated carbon filter 7 through which air can be sucked as carrier gas. The activated carbon filter 7 serves at the same time for the cleaning of the air.

Figure 2:
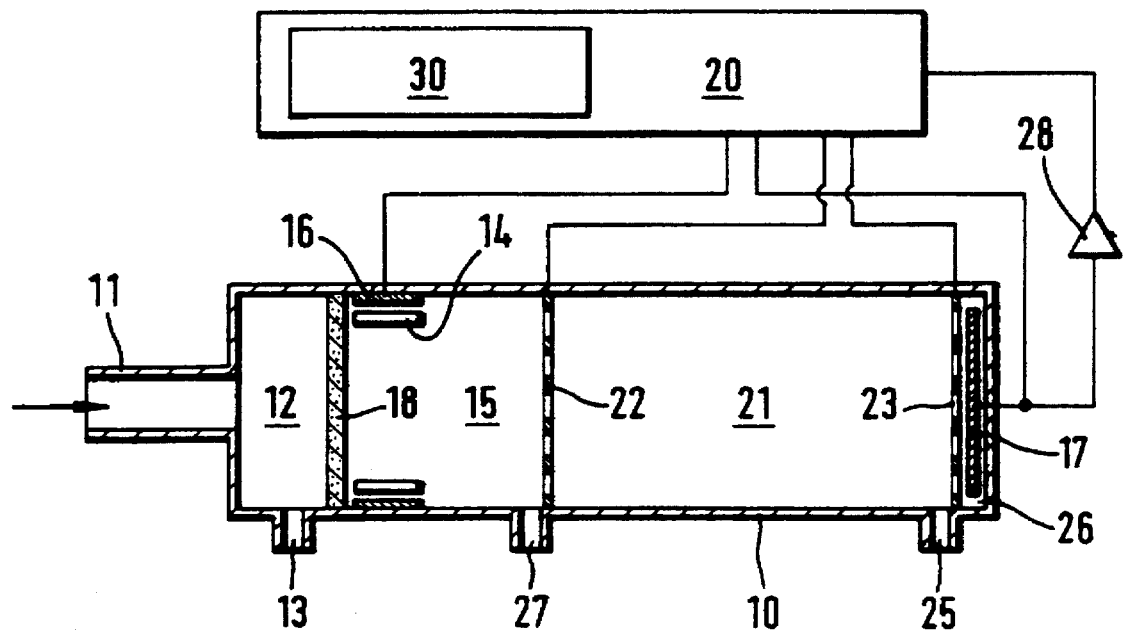
FIG. 2 is a cross-sectional view of an ion mobility spectrometer suitable for the invention.

In FIG. 2 is shown a tube-shaped spectrometer casing 10, having a gas inlet 11 through which the carrier gas, together with the analyte molecules transported therein, is sucked into a membrane-antechamber. The gas pump (not shown) for sucking in the gas is connected to the membrane antechamber 12 via a lateral connection opening 13. Purging gas can optionally also be fed through the lateral connection opening 13, after activation of a solenoid valve (likewise not shown), in order to purge the membrane-antechamber, the gas inlet and the suction head 6 (not shown in FIG. 2). Dried and cleaned air passed through a further filter (not shown) is preferably used for this purpose.

Adjacent to the outlet side of the antechamber 12 is a non-porous (homogeneous) diaphragm 18. Preferably it is made from silicone rubber and mainly is provided avoid entering of water molecules while the indicator molecules can diffuse therethrough. The membrane 18 is adjoined by the reaction chamber 15, whose walls comprise a $Ni^{63}$ source 14 by means of whose -radiation positively charged reaction ions, in particular of the $(H_2O)_nH^+$ type, are formed from the carrier gas. A d.c. voltage which is generated by a high-voltage source in the central processing unit 20 of the device is applied to a positive electrode 16, also provided in the reaction chamber 15, and a collector electrode 17. An electric d.c. field is thus created between the electrodes 16, 17. Preferably this electric field is stabilized at intermediate potentials by additional electrodes (not shown) located between the electrodes 16 and 17.

In the reaction chamber 15 the reaction ions react with the analyte molecules. By charge transfer positively charged product ions are formed. The product ions and any reaction ions still present are accelerated by the electric field in the direction of the collector 17. They pass into the drift chamber 21, which is separated from the reaction chamber 15 by a switching gate 22. At the end of the drift chamber 21 there is provided in front of the collector 17 a screen grid 23, which serves to keep counter-charges generated by the ionic cloud at a defined low level. In the drift chamber 21 the ions pass through a counter current of a drift gas, which is supplied through a drift gas inlet 28 at the collector-side end 26 of the drift chamber 21 and is discharged at a drift gas outlet 27 provided in the reaction chamber 15 in the vicinity of the switching gate 22. The drift gas is also dried and cleaned. It is preferably circulated in a cycle with a pump (not shown) in a volume controlled flow.

In order to perform an analysis, after sufficient purging of the antechamber 12 with purging gas, sample gas is sucked into the membrane-antechamber 12. Molecules of the indicator substance penetrate diaphragm 18 passing into reaction chamber 15 and becoming ionized therein. The switching gate 22 is opened at relatively long time intervals (for example 30 msec) for relatively short periods at a time (for example 800 μsec). At each opening of the gate 22 an ionic cloud passes into the drift chamber 21. The molecules contained therein separate during the drift movement through the drift chamber 21 in accordance with their mobility, with the most rapidly mobile (smallest) molecules arriving at the collector 17 first and the least mobile (largest) molecules last. At the collector 17 the ions are discharged, so that an electric current flows, which is amplified by an amplifier 28 and fed to the central processing unit The latter contains suitable electronic processing elements, in particular in the form of a microcomputer that processes the signals—usually under software control after digitization—and displays the results on a display 30 in graph form or as numerical values. Printing out of the results is naturally also possible.

In practice for the recording of a spectrum the switching gate is opened and closed again many times (for example sixteen times). An ion mobility spectrum is formed by accumulation of the data so obtained.

It is not necessary to explain the IMS measurement method further, because the measuring technique used for the invention is largely conventional. A special feature, in addition to the suction head 6 already mentioned, is that the diaphragm 18 separating the antechamber 12 from the reaction chamber 15 is heated to a relatively high temperature of at least about 60° C., preferably at least about 70° C. The diaphragm helps to improve the selectivity of the spectrometer and suppress unwanted substances. The elevated temperature leads to an increase in measuring speed. This has proved to be particularly advantageous in the analysis of printing inks, where sensitivity and speed are prime requirements.

In order to increase the measuring speed, it may be advantageous to pro-heat the carrier gas that is passed across the surface 3 of the printed article 2 in order to pick up the indicator molecules. Particular energy savings can be made if the gas, which is directed past the hot diaphragm 18 during the purging and thus heated, is on its return path (not shown) pumped across the surface 3 into the suction head 6.

In order to perform a quality control operation the suction head 6 is contacted with its suction opening onto the printed article 5, as was described before (FIG. 1). In the case of a quality control in a non-moving status the connection between the suction opening and the printed article 2 can be made sufficiently tight by placing the latter on a plane support.

Preferably, however, the quality control is performed in on-line-operation, i.e. during the running printing process above the moving printed article. When the printed article is moved at a low speed the suction head 6 can be contacted to the moving printed article and moved therewith during the measurement.

However with higher printing speeds this becomes impractical. In this case a stationary suction head 6 is located closely above the moving printed article 2 in a non-moving manner. In this case according to a preferred embodiment of the invention means are provided at the edge of the suction opening by which penetration of gas which may disturb the measurement from the space outside the suction head into the inner space of the suction head (i.e. via the gap between the edge of the suction head 6 and the printed article 2) is reduced.

Such means can be provided in different manner. In particular the periphery of the suction opening can be provided with a strip of elastic low-friction material such as teflon which is adapted to close the gap as far as possible during the measurement by providing a sealing curtain which is in sliding contact with the printed article 2.

Alternatively a gas curtain may be used in order to avoid penetration of disturbing gas out of the outer space into the inner space of the suction head 6. To this end according to a further preferred embodiment gas jet openings are distributed on the periphery of the suction opening in such a manner that a gas curtain may be generated around the entire periphery of said opening. In practice this may for example be embodied by providing a tube running around the periphery of the suction opening and having openings directed towards the printed article which serve as gas jets. For generation of the gas curtain for example cleaned and dried air oK inert gas may be used.

Figure 3:
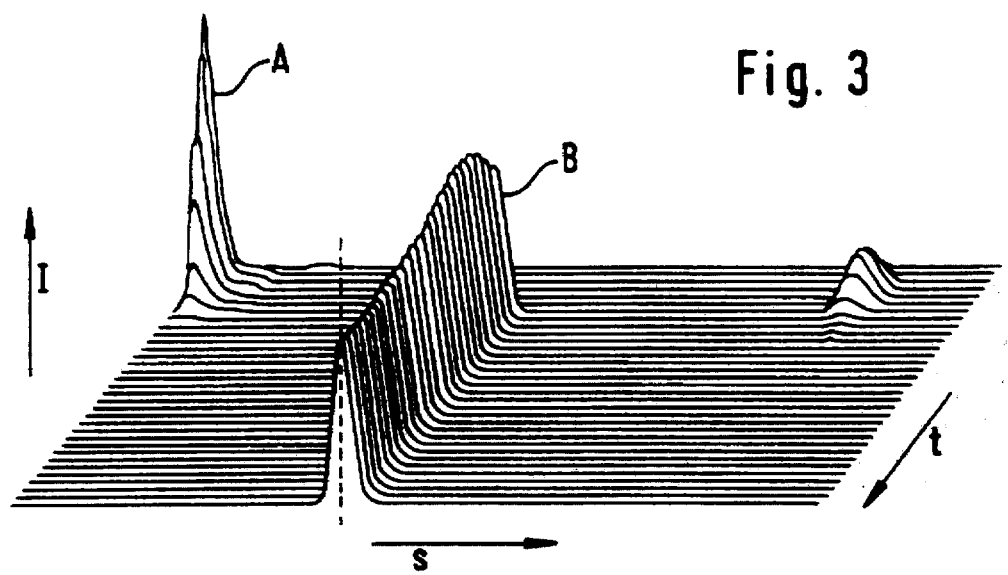
FIG. 3 is a graph of the variation over time of an IMS spectrum measured on a radiation-cured printing ink layer and FIG. 4 is a comparison of measurement results obtained on the one hand with conventional methods and on the other with the invention.

FIG. 3 shows in a three-dimensional graphic representation ion mobility spectra that have been measured on an electron beam-cured rotary offset test print. The printing ink formulation contained, as indicator, 0.5% of the product AGeflexFM2 made by CPS, Cray Valley, U.S.A. The radiation dose used for the curing was 18 kGy.

The figure shows plots of IMS spectra (collector current I versus running time s) measured over a total period of 2 minutes.

The reaction ions originally contained in a closed sample vessel are light and mobile. They therefore produce a large peak A with short running times. If a print sample 50 cm² in size is placed in the sample vessel connected to the ion mobility spectrometer, they react with the indicator within 20 sec. The reaction ion peak A therefore disappears and a product ion peak B is obtained, whose area matches the concentration of the indicator in the ambient air of the print sample. Due to the rapid formation of the product ions and their direct measurability, the indicator concentration can be measured within less than 10 sec. This corresponds to conventional time constants for the adjustment times of printing machines employing radiation-curing printing inks. Consequently the potential of the invention for real-time quality control during the production process is demonstrated.

Figure 4:
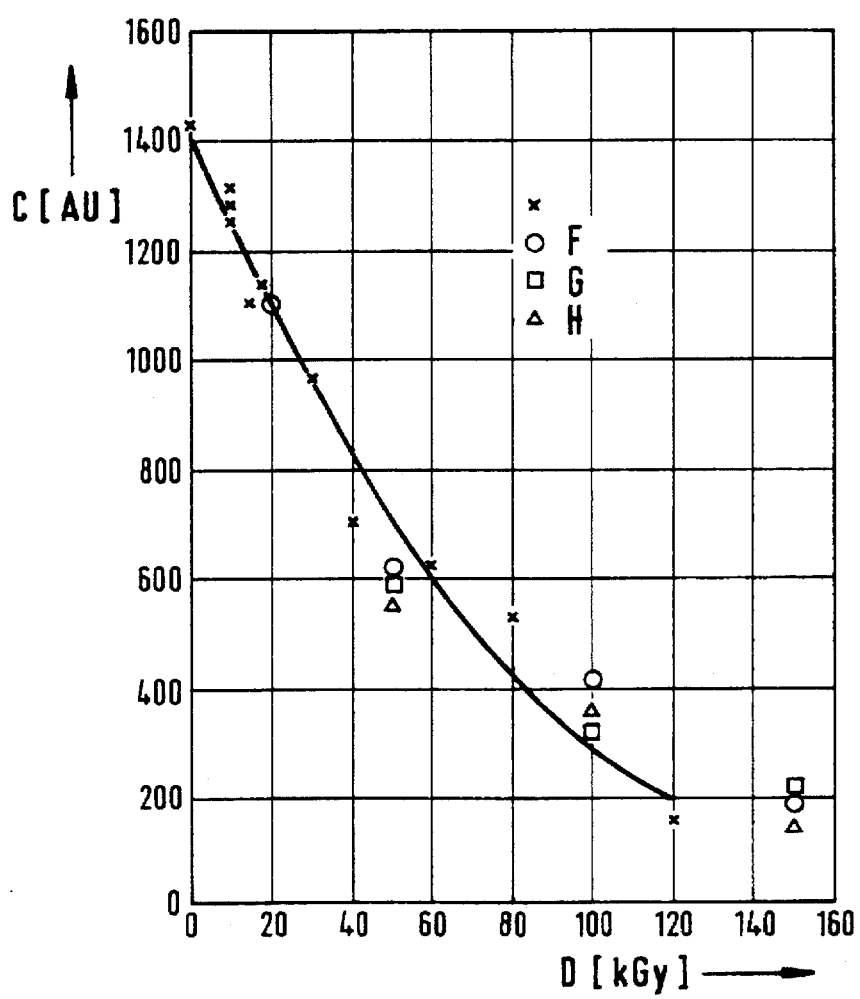

FIG. 4 shows the dose dependency of the IMS indicator peak B. The abscissa shows the radiation dose in kGy, while the peak area, i.e. the indicator concentration in arbitrary units, is given on the ordinate. The crosses represent experimentally determined values of the indicator peak area.

FIG. 4 also contains HPLC analysis values for three typical model binder systems F, G, H, whose composition is given in Table I below.

TABLE 1

| | | Composition in weight percent | | | |
|---|---|---|---|---|---|
| Component | Trade name | Manufacturer | F | G | H |
| TPGDA | TPGDA | UCB | 13.0 | 9.8 | 11.4 |
| TMPTA | TMPTA | UCB | 26.1 | 9.8 | 11.4 |
| HEMA | HEMA | UCB | 4.3 | 1.7 | 1.9 |
| Acrylic acid dimer | β-CEA | UCB | — | 25.0 | — |
| Novolac acrylate | RD202 | UCB | 56.6 | 21.2 | 27.0 |
| Aninoacrylate | Ageflex FA-1 | CPS | — | — | 10.0 |
| Acrylated acrylic | EB1701 | UCB | — | 32.5 | 38.3 |

Composition F corresponds to the binder system of the printing ink on which the measurements shown in FIG. 3 were made.

All the concentration values, both those determined by HPLC for the model substances F, G and H and the peak areas of the IMS indicator, were standardized for a dose of 20 kGy to the same value of the arbitrary scale division (1100).

FIG. 4 shows not only that the three model substances F, G and H have the same characteristic dependence on the radiation dose used for the curing, but that the test results with the method according to the invention show the same functional pattern with comparable measuring accuracy. It is therefore clear that with the invention a quality parameter is measured for the crosslinking of printing ink films that correlates excellently with conventionally determined HPLC values. It involves far less expenditure on equipment, however, and can be directly and non-destructively measured in the production process.

We claim:

1. In a coating process wherein a radiation curable coating composition is applied to a surface and the composition is radiation cured to polymerize and cross-link the composition to form a coating, the improvement comprising the steps of: providing a proton affinitive indicator substance in the composition capable of reacting with other substances in the composition during polymerization and cross-linking of the composition; providing an ion mobility spectrometer having a suction head and a gas inlet, disposing the suction head over the coating; drawing in a sample of gas phase above the coating into the gas inlet; and analyzing the drawn in sample by ion mobility spectroscopy to detect the indicator substance escaping from the coating to thereby indicate a measure of a content of non-cross-linked migrating polymerizable components of the composition in said coating and thereby the degree of curing of the coating process.

2. The method according to claim 1, wherein the coating composition is a printing ink or a lacquer.

3. The method according to claim 1, wherein the indicator substance has a proton affinity greater than the proton affinity of water.

4. The method according to claim 1, wherein the indicator substance has a proton affinity of at least 750 kJ/mol.

5. The method according to claim 1, wherein the indicator substance has a proton affinity of at least 800 kJ/mol.

6. The method according to claim 1, wherein the indicator substance has a concentration in the composition such that equilibrium concentration of the indicator substance in the gas phase above the coating is no greater than 10 mg/m³.

7. The method according to claim 1, wherein the indicator substance has a concentration in the composition such that equilibrium concentration of the indicator substance in the gas phase above the coating is no greater than 1 mg/m³.

8. The method according to claim 1, wherein the indicator substance has a concentration in the composition which is no greater than 2% by weight.

9. The method according to claim 1, wherein the indicator substance has a concentration in the composition which is no greater than 1% by weight.

10. The method according to claim 1, wherein the indicator substance has a concentration in the composition which is no greater than 0.5% by weight.

11. The method according to claim 1, wherein the indicator substance is a polymerization initiating component of the composition.

12. The method according to claim 11, wherein the indicator substance is a photo-initiator.

13. The method according to claim 11, wherein the indicator substance is a co-initiator.

14. The method according to claim 11, wherein the composition includes a second polymerization initiating component having a proton affinity of at least 10% less than the proton affinity of the indicator substance.

15. The method according to claim 1, wherein the indicator substance has a molecular weight of at least 50 and at most 400 grams/mole.

16. The method according to claim 1, wherein the indicator substance is one selected from the group consisting of a benzoin, benzoin ether, thioxanthone derivative, α,α-dialkoxyacetophenone derivative, α-hydroxyalkylphenone, α-aminoalkylphenone derivative, acrylophosphine oxide, benzophenone and a benzophenone derivative.

17. A method according to claim 1, wherein the indicator substance is 2-hydroxy-2-methyl-1-phenyl-propan-1-one.

18. A method according to claim 1, wherein the indicator substance is 1-(4-isopropylphenyl)-2-hydroxy-2-methyl-propan-1-one.

19. The method according to claim 1 wherein the steps of disposing the suction head over the coating and drawing in a sample is performed on-line during a printing process on a printed article.

20. The method according to claim 1, wherein the indicator substance is one selected from the group consisting of an amino acrylate, a copolymerisable amine and an alkyl amine.

21. The method according to claim 1, wherein the indicator substance is benzil ketal.

22. A coating process, comprising the steps of:

applying a radiation curable coating composition to a surface, and radiation curing the composition to polymerize and cross-link the composition to form a coating, wherein the composition includes a proton affinitive indicator substance capable of reacting with other substances in the composition during polymerization and cross-linking of the composition and wherein the indicator substance escaping from the coating is detectable by drawing in a sample of gas phase above the coating and analyzing the drawn in sample by ion mobility spectroscopy to indicate a measure of a content of non-cross-linked migrating polymerizable components of the composition in said coating and thereby the degree of curing of the coating process.

23. The method according to claim 22, further comprising detecting the escaping indicator substance with an ion mobility spectrometer by disposing a suction head of the spectrometer over the coating and communicating the escaping indicator substance from the suction head to a gas inlet of the spectrometer.

24. The method according to claim 23, wherein the step of detecting further comprises communicating the escaping indicator substance from the gas inlet to a reaction chamber of the spectrometer and demarcating an upstream side of the reaction chamber with a diaphragm and heating the diaphragm to a temperature of at least 60° C.

25. The method according to claim 24, wherein the diaphragm is heated to at least 70° C.

26. The method according to claim 23, further comprising providing a strip of elastic material to a periphery of a suction opening of the suction head.

27. The method according to claim 23, further comprising providing a curtain of gas jets around a periphery of a suction opening of the suction head.

* * * * *